US005295192A

United States Patent [19]

Hamada et al.

[11] Patent Number: 5,295,192

[45] Date of Patent: Mar. 15, 1994

[54] ELECTRONIC NOISE ATTENUATION METHOD AND APPARATUS FOR USE IN EFFECTING SUCH METHOD

[75] Inventors: Hareo Hamada, 1-30-7 Nishi-Kubo, Musashino-shi, Tokyo; Tanetoshi Miura, 1-11-20 Minami-cho, Kokubunji-shi, Tokyo; Akio Kinoshita, Fujisawa; Noriharu Sato, Katsuta; Keiichiro Mizuno; Minoru Takahashi, both of Tokyo, all of Japan

[73] Assignees: Hareo Hamada; Tanetoshi Miura; Nissan Motor Co., Ltd.; Hitachi Ltd.; Bridgestone Corporation; Hitachi Plant Engineering & Construction Co., Ltd., Japan

[21] Appl. No.: 957,068

[22] Filed: Oct. 6, 1992

Related U.S. Application Data

[63] Continuation of Ser. No. 670,908, Mar. 18, 1991, abandoned.

[30] Foreign Application Priority Data

Mar. 23, 1990 [JP] Japan .................................. 2-74069

[51] Int. Cl.[5] ......................... A61F 11/06; H04R 3/02

[52] U.S. Cl. ...................................... 381/71; 381/73.1

[58] Field of Search .................... 381/71, 73.1, 13, 93, 381/94

[56] References Cited

U.S. PATENT DOCUMENTS 4,377,793 3/1983 Horna .................................. 381/71
4,473,906 9/1984 Warnaka ............................ 381/73.1
4,683,590 7/1987 Miyoshi ................................. 381/71
4,689,821 8/1987 Salikuddin et al. .................. 381/94
4,783,817 11/1988 Hamada ................................ 381/71
4,947,434 8/1990 Ito ......................................... 381/71
5,018,202 5/1991 Takahashi ............................. 381/71

FOREIGN PATENT DOCUMENTS 0333461 9/1989 .
1-501344 5/1989 Japan .
WO88/02912 4/1988 PCT Int'l Appl. .

*Primary Examiner*—James L. Dwyer
*Assistant Examiner*—Jack Chiang
*Attorney, Agent, or Firm*—Oliff & Berridge

[57] ABSTRACT

A method for electrically attenuating a noise in an area for a sound wave to be propagatable in a three dimensional direction by making up a drive signal from the information on the noise and previously given filter coefficients by use of an adaptive digital filter and then generating an additional sound wave in accordance with the drive signal for cancellation of the noise. In the electric noise attenuation method, there are provided in a given region for noise attenuation, first and second error sensor groups for detecting an interference sound wave produced between the noise and additional sound wave, at a sampling time, a filter coefficient is calculated based on the information relating to the first error sensor group, at the next sampling time, another filter coefficient is calculated based on the information relating to the second error sensor group, and these operations are repeatedly executed sequentially for each error sensor to thereby update the filter coefficient of the adaptive digital filter.

28 Claims, 5 Drawing Sheets

ELECTRONIC NOISE ATTENUATION METHOD AND APPARATUS FOR USE IN EFFECTING SUCH METHOD

This is a continuation of application Ser. No. 07/670,908 filed Mar. 18, 1991, now abandoned.

BACKGROUND OF THE OF THE INVENTION

Field of the Invention

The present invention relates to an electronic noise attenuation method and an apparatus for use in effecting such method and, in particular, to such electronic noise attenuation method which electronically achieves attenuation of a sound wave propagated from a source of noise in an area in which a sound wave can be propagated in a three dimensional direction by generating another sound wave 180° out of phase and the same sound pressure with the propagated sound wave to produce interference between these two sound waves in a given region within the above-mentioned sound propagatable area, and an apparatus for use in effecting such method.

Description of the Related Art

Conventionally, in an electronic noise attenuation apparatus of the above-mentioned type, in a given area in which a noise is to be attenuated, an additional sound which is 180° out of phase and has the same sound pressure with the noise to be attenuated is generated from a speaker and a drive signal for driving the speaker is made up by an adaptive speaker in accordance with inputs from a sensor microphone to detect the noise and the like as well as in accordance with the output of an error sensor to detect the interference sound between the noise and additional sound in the given noise attenuation area.

Referring now to FIG. 4, there is shown a basic structure of the above-mentioned type of conventional electronic noise attenuation apparatus, in which an adaptive digital filter 1 outputs a speaker drive signal y(n) in accordance with an input x(n). In FIG. 4, d(n) designates a desirable response in an error sensor to the input x(n), and e(n) represents an error output to be detected by the error sensor. Also, C designates a transfer function from the sensor to the error sensor.

Now, the adaptive digital filter 1 can be realized by a FIR filter having a variable tap weight (filter coefficient) and an adaptive algorithm to control the FIR filter. The adaptive algorithm, in accordance with information of the input x(n) and the error output e(n), adjusts the filter coefficient of the adaptive digital filter so that the energy of the error output e(n) can be the smallest under some evaluation standard.

The output y(n) of the adaptive digital filter 1 can be given by convolving the input x(n) and a filter coefficient $w_i$ and, therefore, the output y(n) can be expressed by the following equation:

$$y(n) = \sum_{i=0}^{I-1} w_i x(n-i) \quad (1)$$

and the error output e(n) can be expressed as follows:

$$\begin{aligned} e(n) &= d(n) + \sum_{j=0}^{J-1} c_j y(n-j) \\ &= d(n) + \sum_{j=0}^{J-1} c_j \Sigma\, w_I x(n-i-j) \\ &= d(n) + \sum_{i=0}^{I-1} w_I r(n-i) \end{aligned} \quad (2)$$

In the equation (2), the r(n) designates a reference signal which has been filtered and this can be expressed by the following equation:

$$r(n) = \sum_{j=0}^{J-1} c_j x(n-j) \quad (3)$$

For the purpose of simplification, if the following vector expressions R and W are used, $$R = [r(n), r(n-1), \cdots r(n-I+1)]^T$$

$$W = [w_0, w_1, \cdots w_{J-1}]^T$$

then the above-mentioned equation (2) can be expressed by the following equation:

$$e(n) = d(n) + R^T \cdot W \quad (4)$$

Here, if a mean square error (M S E: mean-square error), $[e(n)^2]$ is found, then $$\begin{aligned} J &= E[e(n)^2] \\ &= E[e(n)^2] + 2\, W^T E[R^T d(n)] + W^T E[R^T R] W \end{aligned} \quad (5)$$

can be obtained from the equation (4). This shows that the MSE is a quadratic function of the filter coefficient. The differential of the quadratic function is a linear function and, therefore, if the differential is assumed to be 0, then a solution having the minimum value $J_{min}$ can be found.

Now, in an FX algorithm (Filtered-x LSM algorithm) which is an algorithm in the form of a method of steepest descent, an instantaneous square error e $(n)^2$ itself is used as the estimator of the MSE J to obtain the estimator $\hat{\Delta}_n$ of the gradient Δ ) of J from the following equation:

$$\begin{aligned} \hat{\nabla}_n &= \frac{\partial e(n)^2}{\partial W_n} = 2e(n)\frac{\partial e(n)}{\partial W_n} \\ &= 2R^T e(n) \end{aligned} \quad (6)$$

And, using the above equation $\Delta_n$, the filter coefficient of the adaptive digital filter can be updated recurrently from the following equation:

$$\begin{aligned} W_{n+1} &= W_n + \mu(-\hat{\nabla}_e) \\ &= W_n - 2\mu\, R_n{}^T e(n) \end{aligned} \quad (7)$$

where μ is a positive scalar serving as a parameter to control the magnitude of an amount of correction in each repetition. The above equation (7) means that the filter coefficients are sequentially updated in an opposite direction (in a direction of the steepest descent of an error curve) to the gradient vector ($\hat{\Delta}_n$). If such sequential updating is continued, then at last the MSE reaches the minimum value $J_{min}$ in so that the filter coefficient can have the optimum value.

While in the above-mentioned FX algorithm the description has been given of a case in which the number of the error output e (n) is one, description will be given below of a case in which a plurality of error sensors are provided and thus the number of the error outputs e (n) are plural so as to be able to extend the given area for noise to be attenuated.

Here, as shown in FIG. 5, there are arranged two speakers $S_1$, $S_2$ and two error sensors $E_1$, $E_2$. If the filter coefficients of an adaptive digital filters to output drive signals respectively for driving the speakers $S_1$, $S_2$ are expressed as $W_1$, $W_2$, respectively and the error outputs of the error sensors $E_1$, $E_2$ are expressed as $e=(e_1, e_2)$ then the gradient $\hat{\Delta}_n$ of J can be expressed in the following equation:

$$\hat{\nabla}_n = \frac{\partial e^2}{\partial} = 2e_1\frac{\partial e_1}{\partial} + 2e_2\frac{\partial e_2}{\partial} = 2e_1\begin{bmatrix}\frac{\partial e_1}{\partial W_1}\\ \frac{\partial e_1}{\partial W_2}\end{bmatrix} + 2e_1\begin{bmatrix}\frac{\partial e_2}{\partial W_1}\\ \frac{\partial e_2}{\partial W_2}\end{bmatrix} \quad (8)$$

And, if a control system communication function between the speaker and sensor is expressed as C lm , then a reference signal rlm (n) made up by convolution of the input x (n) and C lm can be expressed by the following equation:

$$r_{lm}(n) = \sum_{j=0}^{J-1} c_{lm}X(n-j)$$

where C lm , as shown in FIG. 5, is a communication function between an error sensor of the l rank and a speaker of the m rank.

And, if the reference signal r lm is defined by the following equation, or, $$r\,lm = [r\,lm\,(n),\ r\,lm\,(n=1),\ \cdots rlm\,(n-j+1)]$$

then the above-mentioned equation (8) can be expressed by the following equation:

$$\hat{\nabla}_n = 2e_1\begin{bmatrix}r_{11}\\ r_{12}\end{bmatrix} + 2e_2\begin{bmatrix}r_{21}\\ r_{22}\end{bmatrix} = 2\left\{\begin{bmatrix}r_{11}\,e_1\\ r_{12}\,e_1\end{bmatrix} + \begin{bmatrix}r_{21}\,e_2\\ r_{22}\,e_2\end{bmatrix}\right\} = 2\begin{bmatrix}r_{11}\ r_{21}\\ r_{12}\ r_{22}\end{bmatrix}\begin{bmatrix}e_1\\ e_2\end{bmatrix} = 2R^Te \quad (9)$$

Therefore, in a MEFX algorithm (or Multiple Error Filtered −x Algorithm), the filter coefficients are to be updated in accordance with the following equation;

$$\overline{W}_{n+1} = \overline{W}_n - 2\,\mu\,R^T e\,(n) \quad (10)$$

An example of the conventional electronic noise attenuation system incorporating such algorithm is disclosed in PCT-Publication of Japanese Patent Laid-open No. 1-501344 (International Publication No. WO88/02912).

As can be understood from comparison between the above mentioned equations (7) and (10), the amount of calculation in the MEFX algorithm to update the filter coefficients of the adaptive digital filter is increased almost in proportion to the number of the error sensors (that is, the number of the error outputs) and, in addition, if the number of the noise sources and speakers (that is, the calculation is required accordingly.

Due to the above-mentioned conditions as well as due to the restrictions involved with costs, the capacity of DSP processors and the like, the use of the conventional noise attenuation system has been so far limited to attenuation of periodically occurring noises or pseudo periodical noises.

SUMMARY OF THE INVENTION

The present invention aims at eliminating the drawbacks found in the above-mentioned prior art electronic noise attenuation systems.

Accordingly, it is an object of the invention to provide an electronic noise attenuation method which is capable of greatly reducing the amount of calculation required for updating the filter coefficients of an adaptive digital filter even when a plurality of error sensors are provided, and an apparatus for use in effecting such method.

In order to attain the above object, according to the invention, there is provided an electronic noise attenuation system which detects noise information on one or more noise sources in an area allowing a sound wave to be propagated in a three dimensional direction, makes up a drive signal for driving additional sound generation means from the above noise information detected by an adaptive digital filter and a previously given filter coefficient, allows the additional sound generation means to generate, with respect to a sound wave propagated from the one or more noise sources, another sound wave about 180° out of phase and having nearly equal sound pressure with the propagated sound wave, and causes sound wave interference between the propagated sound wave and the opposite-phase sound wave in a given region within the above-mentioned sound propagatable area to thereby attenuate the sound wave from the one or more source noise in which there are provided a plurality of error sensors in the above-mentioned given region for detecting an interference sound wave produced between the propagated sound wave from the one or more noise sources and the additional sound wave from the additional sound generation means, the plurality of error sensors are divided into at least a first error sensor group comprising one or more error sensors and a second error sensor group comprising one or more error sensors, when sampling the above-mentioned noise information and the outputs of the above-mentioned plurality of error sensors, in a certain one of such samplings, a filter coefficient to render the output signal of the first error sensor group a minimum is calculated based on only the noise information on the first error sensor group and in accordance with a given algorithm, the thus calculated filter coefficient is used to update the filter coefficient of the above-mentioned adaptive digital filter, in the next sampling, a filter coefficient to render a output signal of the second error sensor group a minimum is calculated based on only the noise information on the second error sensor group and in accordance with a given algorithm, the thus calculated filter coefficient is used to update the filter coefficient of the adaptive digital filter, and the calculation and updating operation is repeatedly carried out sequentially for each of the divided error sensors to thereby update the filter coefficients of the adaptive digital filter.

According to the invention, in the filter coefficient updating process for every sampling, a special attention is paid to the instantaneous error output of a certain error sensor. In other words, since all information relating to such error output is known because the information is determined according to the system structure, the filter coefficient of the adaptive digital filter can be calculated based on the error output and the input indicating a noise and in accordance with a given algorithm, and the thus calculated filter coefficient can be used to update the filter coefficient of the adaptive digital filter. Then, in the next sampling, another error sensor is taken up and a similar algorithm is executed to the above case. That is, the error sensors are scanned one by one to thereby update the filter coefficients (which will hereinafter be referred to as "error scanning").

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Detailed description will hereunder be given of the preferred embodiments of an electronic noise attenuation method according to the invention and an apparatus for use in effecting such method with reference to the accompanying drawings.

Figure 1:
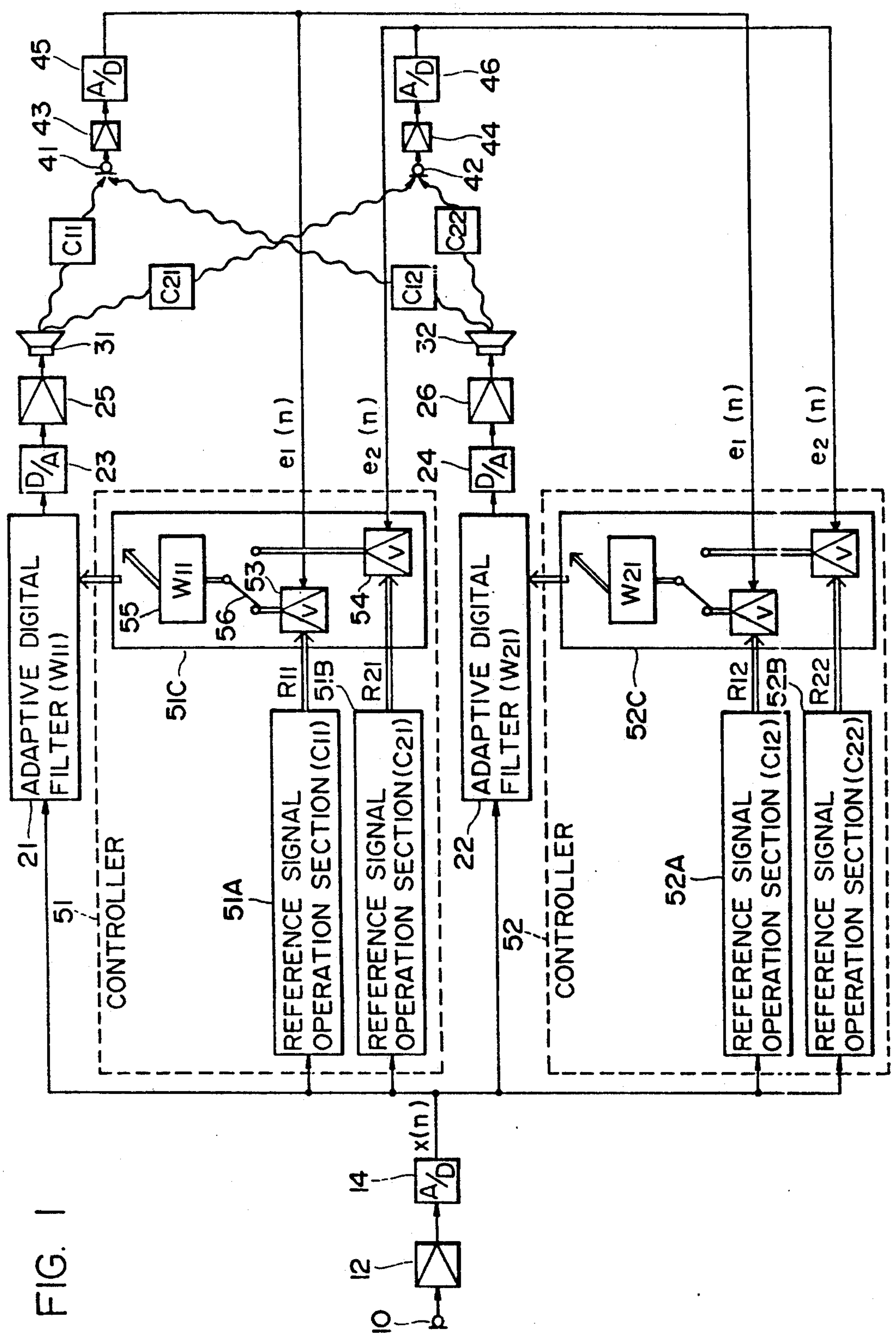
FIG. 1 is a block diagram of an embodiment of an electronic noise attenuation apparatus according to the invention.

Referring firstly to FIG. 1, there is shown a block diagram of an embodiment of an electronic noise attenuation apparatus according to the present invention, including a single noise source, two error sensors, and two secondary sound wave sources (or speakers).

As shown in FIG. 1, the electronic noise attenuation apparatus is mainly composed of a sensor microphone 10, two adaptive digital filters 21, 22, two speakers 31, 32, two error sensors 41, 42 and two controllers 51, 52.

The sensor microphone 10 is used to detect a noise from the noise source and output a signal indicating the detected noise through an amplifier 12 and an A/D converter 14 to the adaptive digital filters 21, 22 and the controllers 51, 52.

The error sensors 41 and 42 are respectively disposed in a given area for noises to be attenuated, and are respectively used to detect a sound wave produced by interference between the noise from the noise source and the additional sound waves from the speakers 31, 32 and output an error signal indicating the interference sound wave through two amplifiers 43, 44 and two A/D converters to the two controllers 51, 52.

The two controllers 51 and 52 are respectively used to calculate filter coefficients $W_{11}$, $W_{21}$ for each sampling in accordance with an error scanning (ES) algorithm and also to update the filter coefficients of the adaptive digital filters 21, 22 by means of the thus calculated filter coefficients $W_{11}$, $W_{21}$, respectively. Also, the controllers 51 and 52 are respectively composed of reference signal operation parts 51A, 51B, 52A, 52B, and ES algorithm execution parts 51C, 52C.

The reference signal operation parts 51A, 51B, 52A and 52B are respectively formed of FIR digital filters having filter coefficients $C_{11}$, $C_{21}$, $C_{12}$, and $C_{22}$ respectively indicating communication functions between the speakers 31, 32 and the error sensors 41, 42. Also, the reference signal operation parts 51A, 51B, 52A and 52B respectively make up reference signals $R_{11}$, $R_{21}$, $R_{12}$ and $R_{22}$ by means of convolving operations by use of an input X(n) indicating each of the noises to be sequentially sampled at a given cycle and the filter coefficients $C_{11}$, $C_{21}$, $C_{12}$ and $C_{22}$ (see the equation (3)), and output these reference signals $R_{11}$, $R_{21}$, $R_{21}$ and $R_{22}$ to the ES algorithm execution parts 51C and 52C.

In the above-mentioned operation, the reference signal operation parts 51A, 52A and 51B, 52B execute their operations alternately for each sampling. Also, in order to identify the coefficient $C_{11}$, the speaker 31 may be previously driven by a pseudo random signal and the output of the FIR digital filter that inputs therein the pseudo random signal is then made to coincide with the error output of error sensor 41. The remaining filter coefficients $C_{21}$, $C_{12}$ and $C_{22}$ are previously identified in a similar manner to the filter coefficient $C_{11}$.

The ES algorithm execution part 51C is used to calculate the filter coefficient $W_{11}$ of the adaptive digital filter 21 according to an adaptive algorithm (that is, ES algorithm) which approximates equivalently to the MEFX algorithm shown by the equation (10) in the adapting process thereof That is, the ES algorithm execution part 51C executes an ES algorithm shown by the following equation in accordance with the above-mentioned reference signals $R_{11}$, $R_{21}$ and error signals $e_1$ (n), $e_2$ (n) which are sampled at a given cycle.

$$\begin{bmatrix} | \\ W_{11} \\ | \end{bmatrix}_{n+1} = \begin{bmatrix} | \\ W_{11} \\ | \end{bmatrix}_{n} - 2\mu \begin{bmatrix} | \\ R_{11} \\ | \end{bmatrix}_{n} e_1(n) \tag{11}$$

$$\begin{bmatrix} | \\ W_{11} \\ | \end{bmatrix}_{n+2} = \begin{bmatrix} | \\ W_{11} \\ | \end{bmatrix}_{n+1} - 2\mu \begin{bmatrix} | \\ R_{21} \\ | \end{bmatrix}_{n+1} e_2(n+1) \tag{12}$$

In other words, at a time (n) of a certain sampling, as shown by the equation (11), the filter coefficient $W_{11}(n+1)$ is calculated in accordance with the filter coefficient $W_{11}(n)$, reference signal $R_{11}$ and error signal $e_1(n)$, and at a time (n+1) of the next sampling, as shown by the equation (12), the filter coefficient $W_{11}(n+2)$ is calculated in accordance with the filter coefficient $W_{11}(n+1)$, reference signal $R_{21}$ and error signal e, (n+1).

As described above, the ES algorithm pays attention to the error signal of one error sensor for each sampling and updates the corresponding filter coefficient based on a reference signal relating to the error signal and according to the FX algorithm. And, at the next sampling, the ES algorithm then pays attention to the error signal of another error sensor and executes a similar updating processing to the above-mentioned case.

Here, in the case of the MEFX algorithm to update the filter coefficient by using a plurality of error signals $e_1(n)$, $e_2(n)$ at the same time, the following equation is used:

$$\begin{bmatrix} | \\ W_{11}R_{21} \\ | \end{bmatrix}_{n+1} e_2(n) = \begin{bmatrix} | \\ W_{11} \\ | \end{bmatrix}_n - 2\mu\left\{\left(\begin{bmatrix} | \\ R_{11} \\ | \end{bmatrix}_n e_1(n) + \right.\right. \qquad (13)$$

the amount of calculation during one sampling period increases almost in proportion to the number of error sensors when compared with the ES algorithm shown by the above-mentioned equation (11) or (12).

Further, in the ES algorithm method, a variable p representing a new time can be defined by the following equation: p= ⌈ n/2 ⌋, where ⌈ · ⌋ represents an integrating operation. As a result of this, the equations (11) and (12) can be expressed approximately as the following equation:

$$\begin{bmatrix} | \\ W_{11}R_{21} \\ | \end{bmatrix}_{p+1} e_2(p) = \begin{bmatrix} | \\ W_{11} \\ | \end{bmatrix}_p - 2\mu \begin{bmatrix} | \\ R_{11} \\ | \end{bmatrix}_p e_1(p) - 2\mu \qquad (14)$$

It can be understood easily that the above-mentioned equation (14) is a good approximate equation to show the behaviors of the ES algorithm method provided that a step size parameter $\mu$ is small enough. The equation (14) is coincident in form with the MEFX that is shown by the equation (13). For this reason, under such a condition that the step size parameter is small enough, it should be understood that the equation (14) converges onto the optimum filter coefficient similarly as in the MEFX.

Now, the ES algorithm execution part 51C includes operation sections 53, 54, 55 and a selection section 56. The operation section 53 calculates the second term of the right side of the equation (11) in accordance with the reference signal $R_{11}$ and the error signal $e_1$ (n) at a certain time (n), and then outputs the resultant to the operation section 55 through the selection section 56. The operation section 55 includes a memory portion for storing the filter coefficient $W_{11}$. The operation section 55 adds the filter coefficient $W_{11}$ stored in the memory section and an output from the selection section 56 to store the resultant stm as a new filter coefficient $W_{11}$ (n+1), and then transfers the filter coefficient $W_{11}$ (n+1) as the filter coefficient of the adaptive digital filter 21 at the next time (n+1) to thereby update the filter coefficient of the adaptive digital filter 21.

Also, the operation section 54, at the next time (n+1), calculates the second term of the right side of the equation (12) in accordance with the $R_{21}$ and the error signal $e_2$ (n+1), and outputs the resultant to the operation section 55 through the selection section 56. Responsive to this, the operation section 55 performs a similar processing to the above-mentioned case to thereby update the filter coefficient of the adaptive digital filter 21.

Likewise, the other ES algorithm execution part 52C performs a similar processing to the above-mentioned ES algorithm execution part 51C to thereby update the filter coefficient of the adaptive digital filter 22.

The adaptive digital filters 21 and 22 respectively convolve the input X(n) and the filter coefficients $W_{11}$ and $W_{21}$ to thereby create drive signals, and then output the drive signals through D/A converters 23, 24 and amplifiers 25, 26 to the speakers 31 and 32, respectively.

In this manner, the speakers 31 and 32 can be driven and the additional sound waves that are produced from the speakers 31 and 32 interfere with the noise in a given region, in which the error sensors 41 and 42 are disposed, so as to be able to attenuate the noise.

The procedure of the above-mentioned ES algorithm will hereunder be described with reference to the flow chart shown in FIG. 6.

Figure 6:
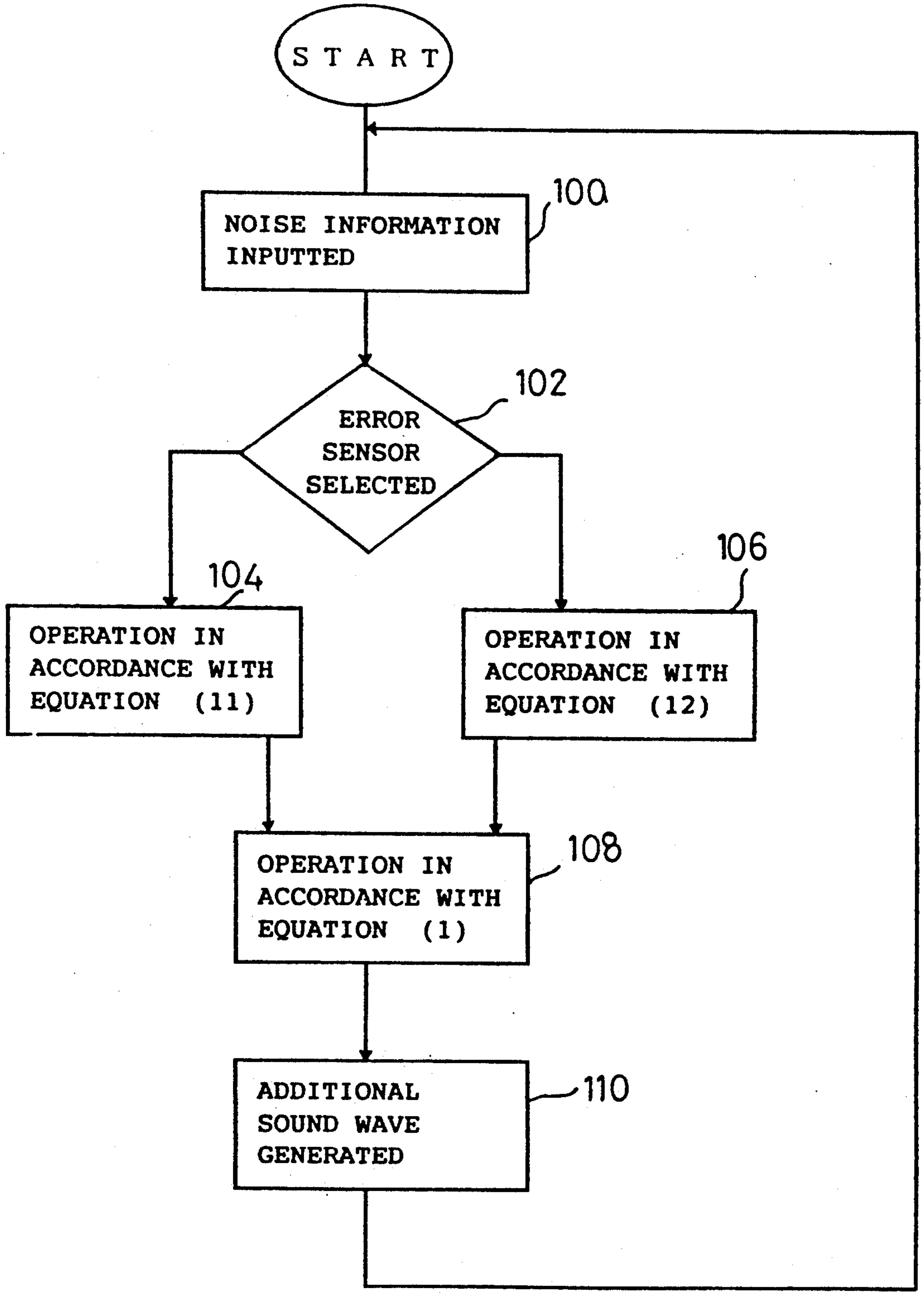

As shown in FIG. 6, first, noise information is inputted at a sampling time (n) (Step 100). Subsequently, either one of two error sensors 41 and 42 is selected. When the error sensor 41 is selected, the routine proceeds to Step 104, and, when the error sensor 42 is selected, the routine proceeds to step 106. Incidentally, at the time n, the error sensor 41 is selected and an error signal $e_1(n)$ is inputted.

In Step 104, a filter coefficient is updated from noise information inputted in Steps 100, 102 and the error signal $e_1(n)$ in accordance with an equation (11). In Step 108, the updated filter coefficient is inputted, a drive signal for speakers 31, 32 (shown in FIG. 1) is calculated from the filter coefficient and the noise information in accordance with an equation (1), and, in Step 110, the speakers 31, 32 are driven in response to the drive signal calculated in Step 108 to produce an additional sound wave, thereby completing the control of one sampling cycle.

Similary, at the time of the succeeding sampling, noise information at a time (n+1) is inputted (Step 100), and, in Step 102, the error sensor 42 is selected and an error signal $e_2(n+1)$ is inputted. Incidentally, since the error sensor 42 is selected, the routine proceeds to Step 106.

In Step 106, a filter coefficient is updated from the noise information inputted in Step 100, 102 and the error signal $e_2(n+1)$ is inputted. Incidentally, since the error sensor 42 is selected, the routine proceeds to Step 106.

In Step 106, a filter coefficient is updated from the noise information inputted in Step 100, 102 and the error signal $e_2(n+1)$ in accordance with an equation (12), the updated filter coefficient is inputted in Step 108, and the drive signal for the speakers 31, 32 is calculated from this filter coefficient and the noise information in accordance with the equation (1). In Step 110, the speakers 31, 32 are driven in response to the drive signal calculated in Step 108 to produce an additional sound wave, thereby completing the following sampling cycle.

As described above, with every sampling, a required error sensor is scanned, and the filter coefficient is updated only from information relating to the error sensor.

Next, description will be given below of a concept relating to the behaviors of the filter coefficient to be updated by the above-mentioned ES algorithm method.

Figure 2:
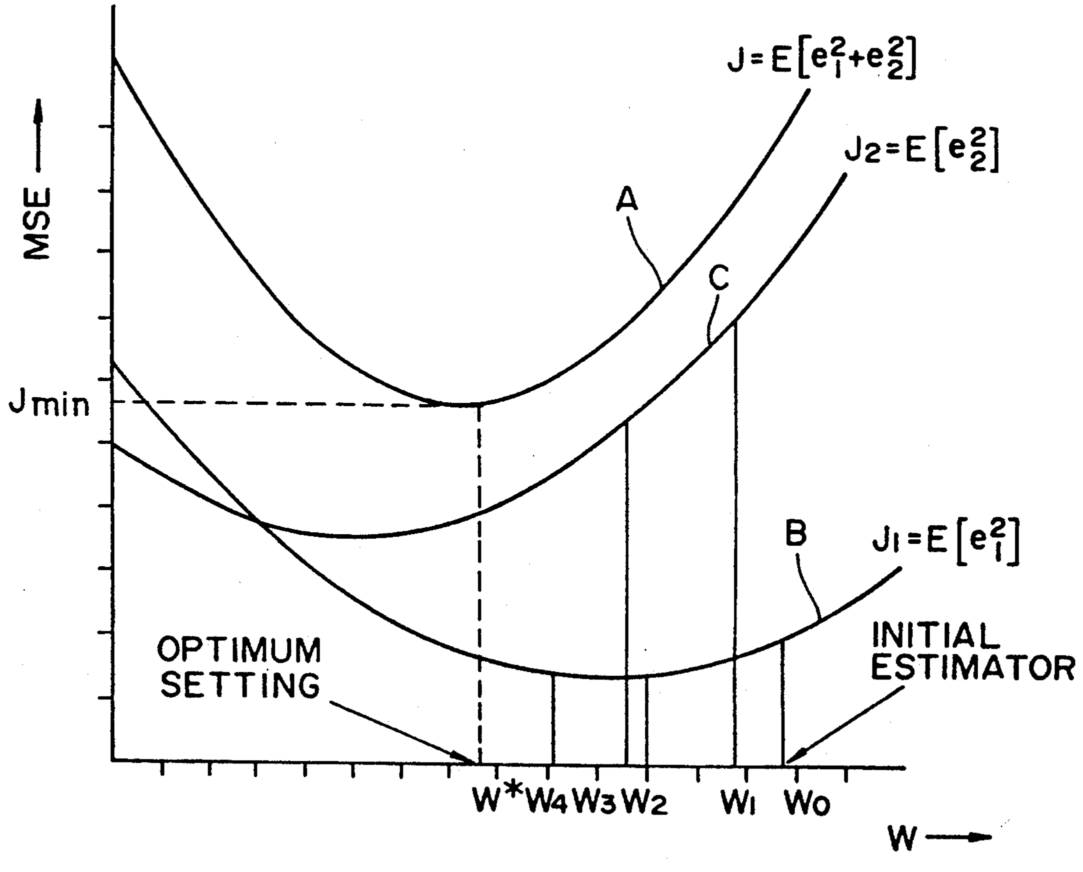
FIG. 2 is a graphical representation used to explain the behaviors of filter coefficients to be updated by an ES algorithm according to the invention.

Referring to FIG. 2, there is shown a graphical representation to illustrate a relation between the filter coefficient W (filter degree first degree). As described before, the MSE can be represented by the quadratic function of the filter coefficient W.

Here, in order to update the filter coefficient in accordance with the MEFX algorithm, the filter coefficient may be updated based on the estimate $\hat{\Delta}_n$ of a local gradient of a curve A indicating $J=E\ [e_1^2+e_2^2]$, whereby the filter coefficient is made to approach gradually to the optimum value corresponding to the minimum value $J_{min}$ of the curve A.

On the other hand, in order to update the filter coefficient in accordance with the ES algorithm, at a certain time, the filter coefficient may be updated based on the estimate $\hat{\Delta}_n$ of a local gradient of a curve B indicating $J_1=E\ [e_1^2]$, at the next time, the filter coefficient may be updated based on the estimate $\hat{\Delta}_n$ of a local gradient of a curve C indicating $J_2=E[e_2^2]$, and at the following times the filter coefficients may be sequentially updated based on the estimates $\hat{\Delta}_n$ to be calculated by switching the curves B and C alternately.

If the filter coefficient is updated on in accordance with the ES algorithm, then the MSE reaches the minimum value $J_{min}$ and the filter coefficient becomes the optimum value, similarly as in the case where the filter coefficient is updated based on the curve A.

The description has been given heretofore of the illustrated embodiment of an electronic noise attenuation apparatus including one noise source, two error sensors and two speakers. However, the invention is not limited to the number of noise sources and the number of speakers, provided that the number of error sensors is two or more.

Figure 3:
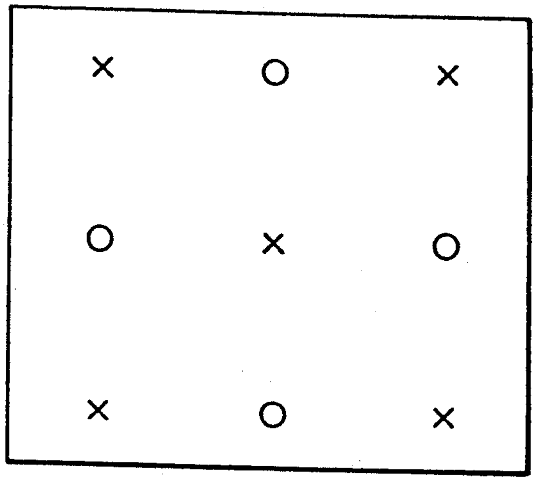
FIG. 3 is a view of an example of the arrangements of error sensors to be error scanned.
Figure 4:
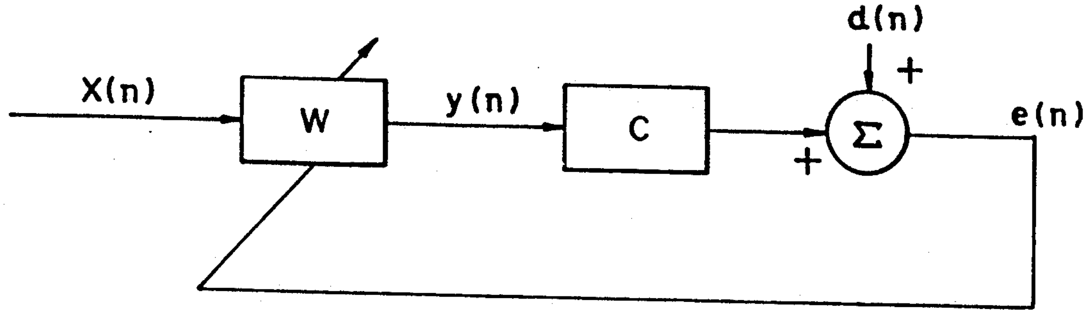
FIG. 4 PRIOR ART
FIG. 4 is a block diagram of a basic structure of an electronic noise attenuation system according to the prior art.
Figure 5:
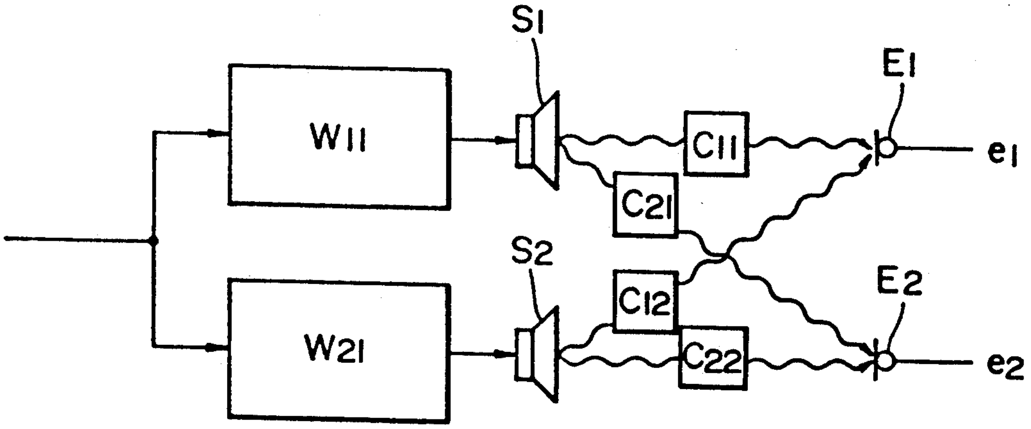
FIG. 5 PRIOR ART
FIG. 5 is a block diagram of the main portions of an electronic noise attenuation apparatus incorporating therein two speakers and two error sensors; and ES algorithm of the present invention.

Also, the number of error sensors to be taken up for each sampling is not limited to one but, for example, as shown in FIG. 3, the error sensors may be divided into a first error sensor group shown by 0 and a second error sensor group shown by X, and the first and second error sensor groups may be scanned sequentially to thereby update the filter coefficients.

Further, for example, assuming that the number of error sensors is 4 (that is, E1, E2, E3 and E4) and a DSP chip is capable of calculating the filter coefficient based on the information as to two error sensors at the same time, according to the ES algorithm of the present invention, the above-mentioned four error sensors can be divided into two groups, that is, (E1, E2) and (E3, E4), and the divided error sensor groups can be scanned alternately to thereby update the filter coefficient.

In addition, assuming that the DSP chip is capable of calculating the filter coefficient based on the information as to three error sensors at the same time, according to the ES algorithm of the present invention, the four error sensors can be divided in the following manner and the divided error sensors can be sequentially scanned to thereby update the filter coefficient:

| | |
|---|---|
| 1.) | (E1, E2, E3), (E4) |
| 2.) | (E1, E2, E3), (E4, E1, E2), (E3, E4, E1), (E2, E3, E4) |
| 3.) | (E1, E2, E3), (E2, E3, E4) |

The above-mentioned division 1.) illustrates a case when the four error sensors are divided into three error sensors and one error sensor. In this case, it can be understood that the DSP chip does not fulfil 100% of its capability when calculating the filter coefficient based on the information as to the one error sensor.

The above-mentioned division 2.) illustrates a case when three error sensors are selected equally out of the four error sensors. In this case, the respective combinations of error sensor groups are sequentially scanned to thereby update the filter coefficient. Four scannings completes one round of the combinations of the error sensors.

The division 3.) illustrates a case when three error sensors are selected unequally out of the four error sensors. In other words, the error sensors E2 and E3 are scanned every time, while the error sensors E1 and E4 are scanned every other time. As a result of this, the error sensors E2 and E3 are more weighted than the error sensors E1 and E4.

The method of dividing a plurality of error sensors is not limited to the illustrated embodiment but other various methods can be employed according to the number of error sensors, arrangements of the error sensors, and the capabilities of the DSP used.

As has been described heretofore, according to the electronic noise attenuation method and apparatus of the present invention, when there are provided a plurality of error sensors, the amount of calculation required for updating the filter coefficient of an adaptive digital filter can be reduced to a great extent. For this reason, even with use of a DSP having the same capability, it is possible to increase the number of noise sources, the number of error sensors and the number of secondary sound wave sources, as well as to expand the processing area.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An electronic noise attenuation method for detecting noise from at least one noise source in an area for a sound wave to be propagatable in a three dimensional direction, and for generation at least one additional sound wave against the sound wave propagated from said at least one noise source, said at least one additional sound wave being generated by at least one additional sound wave generation means and being about 180° out of phase and having nearly equal sound pressure with the propagated sound wave from said at least one noise source, thereby causing the propagated sound wave and at least one additional sound wave to interfere with each other so as to attenuate the propagated sound wave in a given region within the propagatable area, said electronic noise attenuation method comprising the steps of:

(a) arranging in said given region a plurality of error sensors, each error sensor detecting an interference sound produced by interference between said propagated sound wave from said at least one noise source and each additional sound wave from said at least one additional sound wave generation means;

(b) dividing said plurality of error sensors into at least a first error sensor group comprising at least one of the plurality of error sensors and a second error sensor group comprising at least one of the plurality of error sensors, the first error sensor group and the second error sensor group containing different ones of the plurality of error sensors;

(c) detecting and sampling said noise and an output signal from the first error sensor group at a certain sampling time;

(d) calculating a set of first adaptive filter coefficients for at least one adaptive digital filter based on said noise and the output of only the first error sensor group and in accordance with a given algorithm to minimize the output signal of said first error sensor group, and updating the adaptive filter coefficients of each adaptive digital filter of the at least one adaptive digital filter by said set of first adaptive filter coefficients;

(e) detecting and sampling said noise and an output signal from the second error sensor group at a next sampling time;

(f) calculating a set of second adaptive filter coefficients for the at least one adaptive digital filter based on said noise and the output of only the second error sensor group and in accordance with the given algorithm to minimize the output signal of said second error sensor group, and updating the adaptive filter coefficients of each adaptive digital filter of the at least one adaptive digital filter by said set of second adaptive filter coefficients;

(g) repeatedly executing steps (c) through (f) sequentially for each group of said divided plurality of error sensors to thereby update the adaptive filter coefficients of each adaptive digital filter; and h) generating said at least one additional sound wave at every sampling time by producing drive signals to drive each of said at least one additional sound wave generation means by convolution of the detected noise and the updated adaptive filter coefficients.

2. An electronic noise attenuation apparatus for achieving attenuation of a sound wave propagated from at least one noise source in a given region within an area for a sound wave to be propagatable in a three dimensional direction by generating at least one additional sound wave about 180° out of phase and having nearly equal sound pressure with the propagated sound wave to thereby produce sound interference between the propagated sound wave and said at least one additional sound wave in the given region within the propagatable area, said electronic noise attenuation apparatus comprising:

noise detection means for detecting noise from said at least one noise source and converting the noise into an electrical noise signal;

at least one additional sound wave generation means for generating at least one corresponding additional sound wave to cancel said propagated sound wave from the at least one noise source in the given region;

a plurality of error sensors disposed in the given region, each error sensor detecting interference between the propagated sound wave from the at least one noise source and the at least one additional sound wave from the at least one additional sound wave generation means, each error sensor converting the interference into electrical interference signals;

at least one adaptive digital filtering generating a drive signal based on the electrical noise signal and adaptive filter coefficients corresponding to each adaptive digital filter, wherein the drive signal corresponding to each adaptive digital filter drives a corresponding one of said at least one additional sound wave generation means; and control means for sampling the electrical noise signal and the electrical interference signals, for calculating at least first adaptive filter coefficients as a first set and second adaptive filter coefficients as a second set, each of the first set and second set minimizing the electrical interference signals based on electrical signals that are sampled in accordance with a given algorithm in each sampling, and for updating the filter coefficients of each adaptive digital filter of the at least one adaptive digital filter by the first adaptive filter coefficients and the second adaptive filter coefficients, wherein said control means includes means for dividing said plurality of error sensors into at least a first error sensor group comprising at least one error sensor and a second error sensor group comprising at least one error sensor, the means for calculating the first adaptive filter coefficients being based on only the electrical interference relating to said first error sensor group at a first sampling time, the means for calculating the second adaptive filter coefficients being based on only the electrical interference signals relating to said second error sensor group at a next sampling time, and the calculating means repeatedly executing each sampling sequentially.

3. The electronic noise attenuation method according to claim 1, wherein, in each adaptive digital filter, when a tap number of said adaptive digital filter is I, when said noise at sampling times n, n−1, . . . , n−I+1, are x(n), x(n−1), . . . , x(n−I+1), and when previously given filter coefficients are $W_0$, $W_1$, . . . , $W_{I-1}$, the step of repeatedly executing determines a drive signal y(n) in accordance with the following equation, $$y(n) = \sum_{i=0}^{I-1} W_i x(n-i).$$

4. The electronic noise attenuation method according to claim 3, wherein the output signal of the first error sensor group at the sampling time (n) is $e_1(n)$, and the output signal of the second error sensor group at a succeeding sampling time (n+1) is $e_2(n+1)$, . . . , and an output signal of an L-th error sensor group at a sampling time (n+L−1) is $e_L(n+L-1)$, the (g) calculates adaptive filter coefficients of said adaptive digital filter based on successively updating the adaptive filter coefficients W in accordance with the following equations, $$
\begin{aligned}
W_{n+1} &= W_n - 2\mu\, R_1(n)^T e_1(n) \\
W_{n+2} &= W_{n+1} - 2\mu\, R_2(n+1)^T e_2(n+1) \\
&\cdot \\
&\cdot \\
&\cdot \\
W_{n+L} &= W_{n+L-1} - 2\mu\, R_L(n+L-1)^T e_L(n+L-1) \\
W_{n+L+1} &= W_{n+L} - 2\mu\, R_1(n+L)^T e_1(n+L) \\
W_{n+L+2} &= W_{n+L+1} - 2\mu\, R_2(n+L+1)^T e_2(n+L+1) \\
&\cdot \\
&\cdot \\
&\cdot
\end{aligned}
$$

where $\mu$=a step-size parameter,

L=number of error sensor groups, L≧2, $W_n$=adaptive filter coefficients vector at sampling time (n), $R_1$=a reference signal matrix generated from said noise in a first FIR filter having predetermined filter coefficients corresponding to a first transfer function from each additional sound wave generation means to the first error sensor group, $R_2$=a reference signal matrix generated from said noise in a second FIR filter having predetermined filter coefficients corresponding to a second transfer function from each additional sound wave generation means to the second error sensor group, and $R_L$=reference signal matrix generated from said noise in L-th FIR filters having predetermined filter coefficients corresponding to L-th transfer functions from each additional sound wave generation means to the L-th error sensor group.

5. The electronic noise attenuation method according to claim 1, wherein the step of dividing said plurality of error sensors divides said plurality of error sensors into at least the first error sensor group and the second error sensor group so that the adaptive filter coefficients of each of said adaptive digital filters are updated at a uniform update rate.

6. The electronic noise attenuation method according to claim 1, wherein the step of dividing said plurality of error sensors divides said plurality of error sensors into at least the first error sensor group and the second error sensor group such that the adaptive filter coefficients of each of said adaptive digital filters are updated at a non-uniform update rate.

7. The electronic noise attenuation apparatus according to claim 2, wherein, in each adaptive digital filter, when a tap number of said adaptive digital filter is I, when said noise at sampling times n, n−1, . . . , n−I+1, are x(n), x(n−1), . . . , x(n−I+1), and when previously given filter coefficients are $W_0$, $W_1$, . . . , $W_{I-1}$, the control means includes means for determining a drive signal y(n) in accordance with the following equation, $$y(n) = \sum_{i=0}^{I-1} W_i x(n-i).$$

8. The electronic noise attenuation apparatus according to claim 7, wherein the electrical signal output of the first error sensor group at the sampling time (n) is $e_1(n)$, the electrical signal output of the second error sensor group at a succeeding sampling time (n+1) is $e_2(n+1)$, . . . , an electrical signal output of an L-th error sensor group at a sampling time (n+L−1) is $e_L(n+L-1)$, and the control means includes means for successively updating the adaptive filter coefficients W of said adaptive digital filter in accordance with the following equations, $$\begin{aligned}
W_{n+1} &= W_n - 2\mu\, R_1(n)^T e_1(n) \\
W_{n+2} &= W_{n+1} - 2\mu\, R_2(n+1)^T e_2(n+1) \\
&\vdots \\
W_{n+L} &= W_{n+L-1} - 2\mu\, R_L(n+L-1)^T e_L(n+L-1) \\
W_{n+L+1} &= W_{n+L} - 2\mu\, R_1(n+L)^T e_1(n+L) \\
W_{n+L+2} &= W_{n+L+1} - 2\mu\, R_2(n+L+1)^T e_2(n+L+1) \\
&\vdots
\end{aligned}$$

where $\mu$=a step-size parameter,

L=number of error sensor groups, L≧2, $W_n$=adaptive filter coefficients vector at sampling time (n), $R_1$=a reference signal matrix generated from said noise in a first FIR filter having predetermined filter coefficients corresponding to a first transfer function from each additional sound wave generation means to the first error sensor group, $R_2$=a reference signal matrix generated from said noise in a second FIR filter having predetermined filter coefficients corresponding to a second transfer function from each additional sound wave generation means to the second error sensor group, and $R_L$=reference signal matrix generated from said noise in L-th FIR filters having predetermined filter coefficients corresponding to L-th transfer functions from each additional sound wave generation means to the L-th error sensor group.

9. The electronic noise attenuation apparatus according to claim 2, wherein said control means includes a program adapting each of said plurality of error sensors for adapting the adaptive filter coefficients of each of said adaptive digital filters with a uniform update rate.

10. The electronic noise attenuation apparatus according to claim 2, wherein said control means includes a program adapting each of said plurality of error sensors for adapting the adaptive filter coefficients of each of said adaptive digital filters with a non-uniform update rate.

11. An electronic noise attenuation method comprising the steps of:

(a) sampling a noise signal to form a digital noise signal at a present sample time;

(b) generating reference signals based on the digital noise signal at the present sample time and predetermined filter coefficients;

(c) selecting an error signal at the present sample time from a plurality of error signals generated by a plurality of error sensor groups;

(d) generating adaptive filter coefficients for the present sample time based on adaptive filter coefficients of a previous sample time, the reference signals of the present sample time and the selected error signal of the present sample time;

(e) generating separate drive signals for controlling a plurality of sound wave generating means based on the digital noise signal of the present sample time and the generated adaptive filter coefficients of the present sample time, said plurality of sound wave generating means includes a plurality of speakers;

(f) applying the separate drive signals to the plurality of speakers, outputs of the speakers attenuating the noise.

(g) repeating steps (a) through (f) for a subsequent sample time, wherein the error signal selected at the subsequent sample time is from a different error sensor group that the error sensor group used in the present sample time.

12. The electronic noise attenuation method according to claim 11, wherein the drive signal y(n) is determined in accordance with the following equation:

$$y(n) = \sum_{i=0}^{I-1} w_i x(n-i)$$

wherein in each adaptive digital filter,

I=a tap number of said adaptive digital filter;

x(n), x(n−1), . . . , x(n−I+1)=the noise at specific sampling times;

W=($W_0$, $W_1$, . . . , $W_{I-1}$) are current adaptive filter coefficients of the adaptive digital filter based on successively updating in accordance with the following equations:

$$W_{n+1} = W_n - 2\mu\, R_1(n)^T e_1(n)$$
$$W_{n+2} = W_{n+1} - 2\mu\, R_2(n+1)^T e_2(n+1)$$
$$\vdots$$
$$W_{n+L} = W_{n+L-1} - 2\mu\, R_L(n+L-1)^T e_L(n+L-1)$$
$$W_{n+L+1} = W_{n+L} - 2\mu\, R_1(n+L)^T e_1(n+L)$$
$$W_{n+L+2} = W_{n+L+1} - 2\mu\, R_2(n+L+1)^T e_2(n+L+1)$$
$$\vdots$$

where $\mu$=a step-size parameter;

L=number of error sensor groups, $L \geqq 2$;

$e_1(n)$ is an output error signal of a first error sensor group at a sampling time (n);

$e_2(n+1)$ is an output error signal of a second error sensor group at a succeeding sampling time (n+1);

$e_L(n+L-1)$ is an output error signal of an L-th error sensor group at a sampling time (n+L-1);

$R_1$ are reference signals generated from said noise in first FIR filters having predetermined filter coefficients corresponding to transfer functions from each sound wave generation means to the first error sensor group;

are reference signals generated from said noise in second FIR filters having predetermined filter coefficients corresponding to a transfer function from each sound wave generation means to the second error sensor group; and $R_L$ are reference signals generated from said noise in L-th FIR filters having predetermined filter coefficients corresponding to L-th transfer functions from each sound wave generation means to the L-th error sensor group.

13. The electronic noise attenuation method according to claim 11 further comprising a step of dividing said plurality of error sensors divides said plurality of error sensors into at least a first error sensor group and a second error sensor group such that a first update rate of the adaptive digital filters based on one error sensor group and a second update rate based on another error sensor group are substantially equal.

14. The electronic noise attenuation method according to claim 11 further comprising a step of dividing said plurality of error sensors divides said plurality of error sensors into at least a first error sensor group and a second error sensor group such that a first update rate of the adaptive digital filters based on one error sensor group and a second update rate based on another error sensor group are unequal.

15. An electronic noise attenuation apparatus comprising:

a sensor detecting a noise from a noise source and generating a digital noise signal;

a plurality of sound wave generating means each outputting an attenuating wave for attenuating the noise, said plurality of sound wave generating means includes a plurality of speakers;

a plurality of error sensing groups each containing at least one error sensor, each error sensor group generating an error signal in response to the detection of interference between the noise and outputs from the plurality of speakers;

a plurality of adaptive digital filters, each outputting a speaker signal to one of the plurality of speakers based on the digital noise signal and adaptive filter coefficients; and a controller generating the adaptive filter coefficients for each one of the plurality of speakers based on the error signal from one of the plurality of error sensor groups and a reference signal, wherein the reference signal is generated from the digital noise signal and predetermined filter coefficients, and the error signal selected from generating current adaptive filter coefficients is from a different error sensor group than the error sensor group used to generate the previous adaptive filter coefficients.

16. The electronic noise attenuation apparatus according to claim 15, wherein the drive signal y(n) is determined in accordance with the following equation:

$$y(n) = \sum_{i=0}^{I-1} w_i x(n-i)$$

wherein in each adaptive digital filter,

I=a tap number of said adaptive digital filter;

x(n), x(n-1), . . . , x(n-I+1)=the noise at specific sampling times;

$W=(W_0, W_1, \ldots, W_{I-1})$ are current adaptive filter coefficients of the adaptive digital filter based on successively updating in accordance with the following equations:

$$W_{n+1} = W_n - 2\mu\, R_1(n)^T e_1(n)$$
$$W_{n+2} = W_{n+1} - 2\mu\, R_2(n+1)^T e_2(n+1)$$
$$\vdots$$
$$W_{n+L} = W_{n+L-1} - 2\mu\, R_L(n+L-1)^T e_L(n+L-1)$$
$$W_{n+L+1} = W_{n+L} - 2\mu\, R_1(n+L)^T e_1(n+L)$$
$$W_{n+L+2} = W_{n+L+1} - 2\mu\, R_2(n+L+1)^T e_2(n+L+1)$$
$$\vdots$$

where $\mu$=a step-size parameter;

L=number of error sensor groups, $L \geqq 2$;

$e_1(n)$ is an output error signal of a first error sensor group at a sampling time (n);

$e_2(n+1)$ is an output error signal of a second error sensor group at a succeeding sampling time (n+1);

$e_L(n+L-1)$ is an output error signal of an L-th error sensor group at a sampling time (n+L-1);

$R_1$ are reference signals generated from said noise in first FIR filters having predetermined filter coefficients corresponding to transfer functions from each sound wave generation means to the first error sensor group;

are reference signals generated from said noise in second FIR filters having predetermined filter coefficients corresponding to a transfer function from each sound wave generation means to the second error sensor group; and $R_L$ are reference signals generated from said noise in L-th FIR filters having predetermined filter coefficients corresponding to L-th transfer functions from each sound wave generation means to the L-th error sensor group.

17. The electronic noise attenuation apparatus according to claim 15, further comprising step of dividing said plurality of error sensors divides said plurality of error sensors into at least a first error sensor group and a second error sensor group such that an update rate of the adaptive digital filters based on one error sensor group and an update rate based on another error sensor group is constant.

18. The electronic noise attenuation apparatus according to claim 15, further comprising step of dividing said plurality of error sensors divides said plurality of error sensors into at least a first error sensor group and a second error sensor group such that an update rate of the adaptive digital filters based on one error sensor group and an update rate based on another error sensor group is variable.

19. An electronic noise attenuation method for detecting noise from at least one noise source, and for generating at least one additional vibration wave against the vibration wave propagated from said at least one noise source to an object, the at least one additional vibration wave being generated by at least one additional vibration wave generation means and being about 180° out of phase and having substantially equal amplitude with the propagated vibration wave from the at least one noise source, thereby causing the propagated vibration wave and the at least one additional vibration wave to interfere with each other so as to attenuate the propagated vibration wave, said electronic vibration attenuation method comprising the steps of:

(a) arranging on said object a plurality of error sensors, each error sensor detecting an interference vibration produced by interference between said propagated vibration wave from said at least one noise source and each additional vibration wave from said at least one additional vibration wave generation means;

(b) dividing said plurality of error sensors into at least a first error sensor group comprising at least one of the plurality of error sensors and a second error sensor group comprising at least one of the plurality of error sensors, the first error sensor group and the second error sensor group containing different error sensors of the plurality of error sensors;

(c) detecting and sampling said noise and an output signal from the first error sensor group at a present sampling time;

(d) calculating a set of first adaptive filter coefficients for at least one adaptive digital filter based on said noise and the output of only the first error sensor group and in accordance with a given algorithm to minimize the output signal of said first error sensor group, and updating the adaptive filter coefficients of each adaptive digital filter of the at least one adaptive digital filter by said set of first adaptive filter coefficients;

(e) detecting and sampling said noise and an output signal from the second error sensor group at a next sampling time;

(f) calculating a set of second adaptive filter coefficients for the at least one adaptive digital filter based on said noise and the output of only the second error sensor group and in accordance with the given algorithm to minimize the output signal of said second error sensor group, and updating the adaptive filter coefficients of each adaptive digital filter of the at least one adaptive digital filter by said set of second adaptive filter coefficients;

(g) repeatedly executing steps (c) through (f) sequentially for each group of said divided plurality of error sensors to thereby update the adaptive filter coefficients of each adaptive digital filter; and (h) generating the at least one additional vibration wave at every sampling time by producing drive signals to drive each of said at least one additional vibration wave generation means by convolution of the detected noise and updated filter coefficients.

20. The electronic vibration attenuation method according to claim 19, wherein, in each adaptive digital filter, when a tap number of said adaptive digital filter is I, when said noise at sampling times, n, n−1, . . . , n−I+1, are x(n), x(n−1), . . . , x(n−I+1), and when previously given filter coefficients are $w_0$, $w_1$, . . . , $w_{I-1}$, the step of repeatedly executing determines a drive signal y(n) in accordance with the following equation, $$y(n) = \sum_{i=0}^{I-1} w_i x(n-i).$$

21. The electronic vibration attenuation method according to claim 20, wherein the output signal of the first error sensor group at the sampling time (n) is $e_1(n)$, the output signal of the second error sensor group at a succeeding sampling time (n+1) is $e_2(n+1)$, . . . , an output signal of an L-th error sensor group at a sampling time (n+L−1) is $e_L(n+L-1)$, and step (g) calculates adaptive filter coefficients of said adaptive digital filter based on successively updating the adaptive filter coefficients W in accordance with the following equations, $$\begin{aligned}
W_{n+1} &= W_n - 2\mu\, R_1(n)^T e_1(n) \\
W_{n+2} &= W_{n+1} - 2\mu\, R_2(n+1)^T e_2(n+1) \\
&\vdots \\
W_{n+L} &= W_{n+L-1} - 2\mu\, R_L(n+L-1)^T e_L(n+L-1) \\
W_{n+L+1} &= W_{n+L} - 2\mu\, R_1(n+L)^T e_1(n+L) \\
W_{n+L+2} &= W_{n+L+1} - 2\mu\, R_2(n+L+1)^T e_2(n+L+1) \\
&\vdots
\end{aligned}$$

where $\mu$=a step-size parameter,

L=number of error sensor groups, L≧2, $W_n$=adaptive filter coefficients vector at sampling time (n), $R_1$=reference signal matrix generated from said noise in first FIR filter having predetermined filter coefficients corresponding to a first transfer function from each additional vibration wave generation means to the first error sensor group, $R_2$=reference signal matrix generated from said noise in second FIR filter having predetermined filter coefficients corresponding to a second transfer functions from each additional vibration wave generation means to the second error sensor group; and $R_L$=reference signal matrix generated from said noise in L-th FIR filters having predetermined filter coefficients corresponding to L-th transfer functions from each additional vibration wave generation means to the L-th error sensor group.

22. The electronic vibration attenuation method according to claim 19, wherein the step of dividing said plurality of error sensors divides said plurality of error sensors into at least the first error sensor group and the second error sensor group so that the adaptive filter coefficients of each of said adaptive digital filters are updated at a uniform update rate.

23. The electronic vibration attenuation method according to claim 19, wherein the step of dividing said plurality of error sensors divides said plurality of error sensors into at least the first error sensor group and the second error sensor group so that the adaptive filter coefficients of each of said adaptive digital filters are updated at a variable update rate.

24. An electronic noise attenuation apparatus for achieving attenuation of a vibration wave propagated from at least one noise source to an object by generating at least one additional vibration wave about 180° out of phase and having nearly equal amplitude with the propagated vibration wave to produce vibration interference between the propagated vibration wave and said at least one additional vibration wave, said electronic vibration attenuation apparatus comprising:

noise detection means for detecting noise from the at least one noise source and converting the noise into an electrical noise signal;

at least one additional vibration wave generation means for generating corresponding at least one additional vibration wave to cancel said propagated vibration wave propagating from the at least one noise source to the object;

a plurality of error sensors disposed on the object, each error sensor detecting interference between the propagated vibration wave from the at least one noise source and the at least one additional vibration wave from the at least one additional vibration wave generation means, each error sensor converting the interference into electrical interference signals;

at least one adaptive digital filter generating a drive signal based on the electrical noise signal and adaptive filter coefficients corresponding to each adaptive digital filter, wherein the drive signal corresponding to each adaptive digital filter drives a corresponding one of the at least one additional vibration wave generation means; and control means for sampling the electrical noise signal and the electrical interference signals, for calculating at least first adaptive filter coefficients as a first set and second adaptive filter coefficients as a second set, such that each of the first set and second set minimize the electrical interference signals based on electrical signals that are sampled in accordance with a given algorithm in each sampling, and for updating the filter coefficients of each adaptive digital filter of the at least one adaptive digital filter by the first adaptive filter coefficients and the second adaptive filter coefficients, wherein said control means includes means for dividing said plurality of error sensors into at least a first error sensor group comprising at least one error sensor and a second error sensor group comprising at least one error sensor, the means for calculating the first adaptive filter coefficients being based on only the electrical interference signals relating to said first error sensor group at a first sampling time, the means for calculating the second adaptive filter coefficients being based on only the electrical interference signals relating to said second error sensor group at a next sampling time, and the calculating means repeatedly executing each sampling sequentially.

25. The electronic vibration attenuation apparatus according to claim 24, wherein, in each adaptive digital filter, when a tap number of said adaptive digital filter is I, when said noise at sampling times N, n−1, . . . , n−I+1, are x(n), x(n−1), . . . , x(n−I+1), and when previously given filter coefficients are $w_0$, $w_1$, . . . , $w_{I-1}$, the control means for determining a drive signal y(n) is accordance with the following equation, $$y(n) = \sum_{i=0}^{I-1} w_i x(n-i).$$

26. The electronic vibration attenuation apparatus according to claim 25, wherein the electrical signal output of the first error sensor group at the sampling time (n) is $e_1(n)$, the electrical signal output of the second error sensor group at a succeeding sampling time (n+1) is $e_2(n+1)$, . . . , an electrical signal output of an L-th error sensor group at a sampling time (n+L−1) is $e_L(n+L-1)$, and the control means includes means for successively updating the adaptive filter coefficients W of said adaptive digital filter in accordance with the following equations, $$\begin{aligned}
W_{n+1} &= W_n - 2\mu\, R_1(n)^T e_1(n)\\
W_{n+2} &= W_{n+1} - 2\mu\, R_2(n+1)^T e_2(n+1)\\
&\vdots\\
W_{n+L} &= W_{n+L-1} - 2\mu\, R_L(n+L-1)^T e_L(n+L-1)\\
W_{n+L+1} &= W_{n+L} - 2\mu\, R_1(n+L)^T e_1(n+L)\\
W_{n+L+2} &= W_{n+L+1} - 2\mu\, R_2(n+L+1)^T e_2(n+L+1)\\
&\vdots
\end{aligned}$$

where $\mu$=a step-size parameter,

L=number of error sensor groups, L≧2, $W_n$=adaptive filter coefficients vector at sampling time (n), $R_1$=reference signal matrix generated from said noise in a first FIR filter having predetermined filter coefficients corresponding to a first transfer functions from each additional vibration wave generation means to the first error sensor group, $R_2$=reference signal matrix generated from said noise in a second FIR filter having predetermined filter coefficients corresponding to a second transfer functions from each additional vibration wave generation means to the second error sensor group; and $R_L$=reference signal matrix generated from said noise in L-th FIR filters having predetermined filter coefficients corresponding to L-th transfer functions from each additional vibration wave generation means to the L-th error sensor group.

27. The electronic vibration attenuation apparatus according to claim 24, wherein said control means includes means for adapting each of said plurality of error sensors for updating the filter coefficients of each of said adaptive digital filters with a uniform update rate.

28. The electronic vibration attenuation apparatus according to claim 24, wherein said control means includes means for adapting each of said plurality of error sensors for updating the filter coefficients of each of said adaptive digital filters with a variable update rate.

* * * * *